(12) United States Patent
Vargas et al.

(10) Patent No.: US 10,709,523 B2
(45) Date of Patent: Jul. 14, 2020

(54) THIN FILM TANTALUM COATING FOR MEDICAL IMPLANTS

(71) Applicant: Zimmer, Inc., Warsaw, IN (US)

(72) Inventors: Joseph R. Vargas, Garnerville, NY (US); Steven Seelman, Montclair, NJ (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 16/028,894

(22) Filed: Jul. 6, 2018

(65) Prior Publication Data

US 2018/0325632 A1    Nov. 15, 2018

Related U.S. Application Data

(63) Continuation of application No. 13/933,836, filed on Jul. 2, 2013, now Pat. No. 10,039,619.
(Continued)

(51) Int. Cl.
| | |
|---|---|
| *A61C 8/00* | (2006.01) |
| *A61K 6/04* | (2006.01) |
| *A61K 6/02* | (2006.01) |
| *A61C 13/00* | (2006.01) |
| *C23C 16/14* | (2006.01) |

(Continued)

(52) U.S. Cl.
CPC ........ *A61C 8/0013* (2013.01); *A61C 13/0006* (2013.01); *A61K 6/0205* (2013.01); *A61K 6/04* (2013.01); *A61L 27/06* (2013.01); *A61L 27/306* (2013.01); *C23C 16/14* (2013.01); *C23C 16/405* (2013.01); *C23C 16/46* (2013.01); *A61F 2/28* (2013.01); *A61L 2420/02* (2013.01); *Y10T 428/31678* (2015.04)

(58) Field of Classification Search
CPC .............. A61C 8/0013; A61C 13/0006; A61K 6/0205; A61K 6/04; A61L 27/06; A61L 27/306; C23C 16/14; C23C 16/405; C23C 16/46
See application file for complete search history.

(56) References Cited

U.S. PATENT DOCUMENTS

| | | | |
|---|---|---|---|
| 3,549,847 A | 12/1970 | Clark et al. | |
| 4,123,571 A | 10/1978 | Balog et al. | |
| (Continued) | | | |

FOREIGN PATENT DOCUMENTS

| | | |
|---|---|---|
| EP | 1916007 A1 | 4/2008 |
| WO | WO-03093530 A1 | 11/2003 |
| WO | WO-2014008293 A1 | 1/2014 |

OTHER PUBLICATIONS

"U.S. Appl. No. 13/933,836, Final Office Action dated Sep. 28, 2016", 11 pgs.
(Continued)

*Primary Examiner* — Dah-Wei D. Yuan
*Assistant Examiner* — Andrew J Bowman
(74) *Attorney, Agent, or Firm* — Schwegman Lundberg & Woessner, P.A.

(57) ABSTRACT

A method of depositing a relatively thin film of bioinert material onto a surgical implant substrate, such as a dental implant. Chemical vapor deposition (CVD) may be used to deposit a layer of tantalum and/or other biocompatible materials onto a solid substrate comprised of an implantable titanium alloy, forming a biofilm-resistant textured surface on the substrate while preserving the material properties and characteristics of the substrate, such as fatigue strength.

15 Claims, 11 Drawing Sheets

Related U.S. Application Data

(60) Provisional application No. 61/667,043, filed on Jul. 2, 2012.

(51) Int. Cl.

| | | |
|---|---|---|
| *C23C 16/46* | (2006.01) | |
| *A61L 27/06* | (2006.01) | |
| *A61L 27/30* | (2006.01) | |
| *C23C 16/40* | (2006.01) | |
| *A61F 2/28* | (2006.01) | |

(56) References Cited

U.S. PATENT DOCUMENTS

| 5,282,861 | A | 2/1994 | Kaplan |
| 10,039,619 | B2 | 8/2018 | Vargas et al. |
| 2009/0280248 | A1 | 11/2009 | Goodman et al. |
| 2014/0004356 | A1 | 1/2014 | Vargas et al. |

OTHER PUBLICATIONS

"U.S. Appl. No. 13/933,836, Non Final Office Action dated Mar. 11, 2016", 11 pgs.
"U.S. Appl. No. 13/933,836, Non Final Office Action dated Sep. 3, 2015", 10 pgs.
"U.S. Appl. No. 13/933,836, Non Final Office Action dated Oct. 6, 2017", 4 pgs.
"U.S. Appl. No. 13/933,836, Notice of Allowability dated May 18, 2017", 6 pgs.
"U.S. Appl. No. 13/933,836, Notice of Allowability dated Jun. 12, 2017", 6 pgs.
"U.S. Appl. No. 13/933,836, Notice of Allowance dated Mar. 31, 2017", 9 pgs.
"U.S. Appl. No. 13/933,836, Notice of Allowance dated Apr. 5, 2018", 8 pgs.
"U.S. Appl. No. 13/933,836, Preliminary Amendment filed Oct. 18, 2013", 5 pgs.
"U.S. Appl. No. 13/933,836, Response filed Jan. 25, 2017 to Final Office Action dated Sep. 28, 2016", 11 pgs.
"U.S. Appl. No. 13/933,836, Response filed May 12, 2015 to Restriction Requirement dated Mar. 27, 2015", 6 pgs.
"U.S. Appl. No. 13/933,836, Response filed Jun. 13, 2016 to Non Final Office Action dated Mar. 11, 2016", 11 pgs.
"U.S. Appl. No. 13/933,836, Response filed Dec. 3, 2015 to Non Final Office Action dated Sep. 3, 2015", 13 pgs.
"U.S. Appl. No. 13/933,836, Response filed Dec. 4, 2017 to Non Final Office Action dated Oct. 6, 2017", 7 pgs.
"U.S. Appl. No. 13736738.9, Response filed May 22, 2017 to Non Final Office Action dated Jan. 18, 2017", 12 pgs.
"European Application Serial No. 13/933,836, Restriction Requirement dated Mar. 27, 2015", 6 pgs.
"European Application Serial No. 13736738.9, Non Final Office Action dated Jan. 18, 2017", 5 pgs.
"International Application Serial No. PCT/US2013/049131, International Preliminary Report on Patentability dated Jan. 15, 2015", 10 pgs.
"International Application Serial No. PCT/US2013/049131, International Search Report dated Aug. 22, 2013", 4 pgs.
"International Application Serial No. PCT/US2013/049131, Written Opinion dated Aug. 22, 2013", 8 pgs.
"User Guide—Answers to most questions about: Danfoss Tantalum Coating", Danfoss Tantalum Technologies, [Online] Retrieved From Internet: <http://www.tantalum-coating.com/Literat/UserGuide.pdf>, (May 1, 2005), 1-8.
Balla, et al., "Direct Laser Processing of a Tantalum Coating on Titanium for Bone Replacement Structures", Acta Biomaterialia, vol. 6, (2010), 2329-2334.
Balla, V. K., et al., "Porous tantalum structures for bone implants: Fabrication, mechanical and in vitro biological properties", Acta Biomaterialia, 6, (2010), 3349-3359.
Balla, V. K., et al., "Tantalum—A Bioactive Metal for Implants", JOM, Biological and Biomedical Materials, vol. 62, No. 7, (Jul. 2010), 61-64.
Patel, et al., "Control of Crystalline Phase of Tantalum Deposited on Steel by Magnetron Sputtering", New Jersey Institute of Technology, [Online]. Retrieved from the Internet: <electrochem.org/dl/ma/201/pdfs/0044.pdf>, (2002), 1 pg.
Smith, Matthew T, "Design and development of a silicon carbide chemical vapor deposition reactor", University of South Florida Scholar Commons, [Online]. Retrieved from the Internet: http://scholarcommons.usf.edu/etd /1480, (2003), 87 pgs.
"Canadian Application Serial No. 2,880,824, Office Action dated Jul. 12, 2018", 4 pgs.
"Canadian Application Serial No. 2,880,824, Response filed Jan. 8, 2019 to Office Action dated Jul. 12, 2018", 9 pgs.

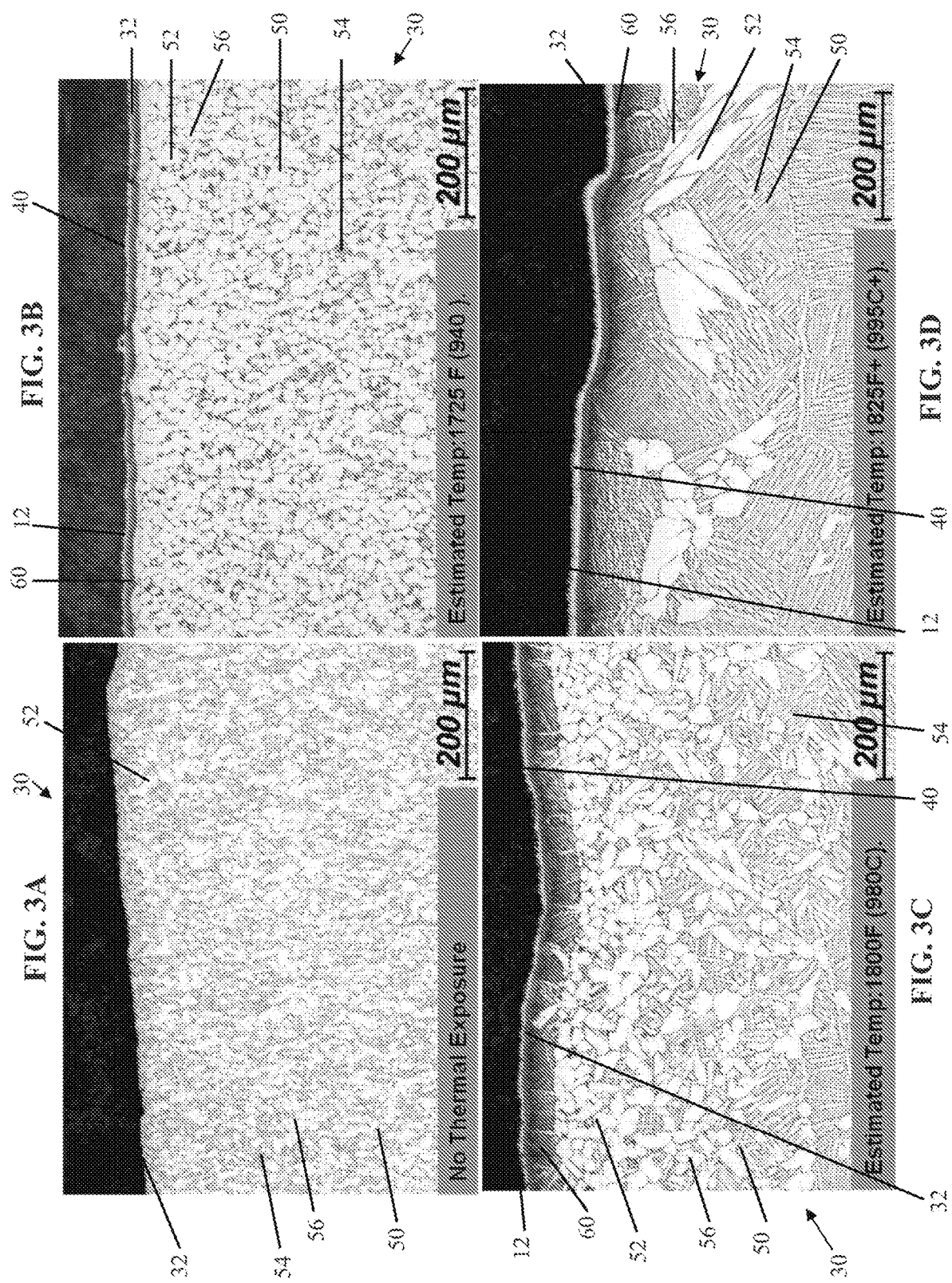

«THIN FILM TANTALUM COATING FOR MEDICAL IMPLANTS»

CLAIM OF PRIORITY

This application is a continuation of U.S. patent application Ser. No. 13/933,836, filed on Jul. 2, 2013, which claims the benefit of U.S. Provisional Patent Application Ser. No. 61/667,043, filed on Jul. 2, 2012 each of which is incorporated by reference herein in its entirety.

FIELD OF THE DISCLOSURE

The present disclosure relates to a method of depositing a relatively thin film of bioinert material onto a medical implant substrate. In one embodiment, the present disclosure relates to a method of depositing tantalum onto a titanium implant via a chemical vapor deposition process while minimizing the deleterious processing temperature effects on the characteristics and properties of the titanium implant substrate material.

BACKGROUND

Orthopedic implants are commonly used to replace some or all of a patient's bone following deterioration due to aging, illness, and/or injury. Implants are often comprised of metal or metal alloy substrates having bioinert or biocompatible characteristics, such as stainless steel, titanium, titanium alloys, or cobalt-chromium alloys. For example, titanium alloys typically have little or no negative reaction with the body tissue surrounding the implant and are corrosion-resistant.

In some instances, it may be desired to provide an implant with a textured surface to inhibit the formation of a biofilm on the surface of the implant and the proliferation of human biologic cells following implantation. In particular, some studies have suggested that implants having textured surfaces may hinder the colonization or aggregation of bacteria cells and, therefore, inhibit the formation of a biofilm and enhance biological cell apposition and attachment for biological fixation and longevity.

SUMMARY

The present disclosure relates to a method of depositing a relatively thin film of bioinert material onto a surgical implant substrate, such as a dental implant. Chemical vapor deposition (CVD) may be used to deposit a layer of tantalum and/or other biocompatible materials onto a solid substrate comprised of an implantable titanium alloy, forming a textured biocompatible surface on the substrate, while preserving the material properties and characteristics of the substrate, such as fatigue strength.

An exemplary method for depositing a bioinert metal or metal alloy onto an implant substrate is provided, including the steps of providing the implant substrate within a reaction chamber; and depositing the bioinert metal or metal alloy onto the implant substrate at a temperature of 800° C.-900° C.

BRIEF DESCRIPTION OF THE DRAWINGS

The above-mentioned and other features of this disclosure, and the manner of obtaining them, will become more apparent and will be better understood by reference to the following description of the embodiments taken in conjunction with the accompanying drawings.

FIG. 3A is a micrograph of a Ti64 substrate that has not been heat treated or coated;

FIG. 3B is a micrograph of a Ti64 substrate having a tantalum coating produced by a 10-hour chemical vapor deposition (CVD) cycle at 940° C.;

FIG. 3C is a micrograph of the Ti64 substrate having a tantalum coating produced by a 10-hour CVD cycle at 980° C.;

FIG. 3D is a micrograph of the Ti64 substrate having a tantalum coating produced by a 10-hour CVD cycle at a temperature of at least 995° C.;

Corresponding reference characters indicate corresponding parts throughout the several views. The exemplifications set out herein illustrate embodiments of the disclosure, and such exemplifications are not to be construed as limiting the scope of the disclosure in any manner.

DETAILED DESCRIPTION

Figure 2:
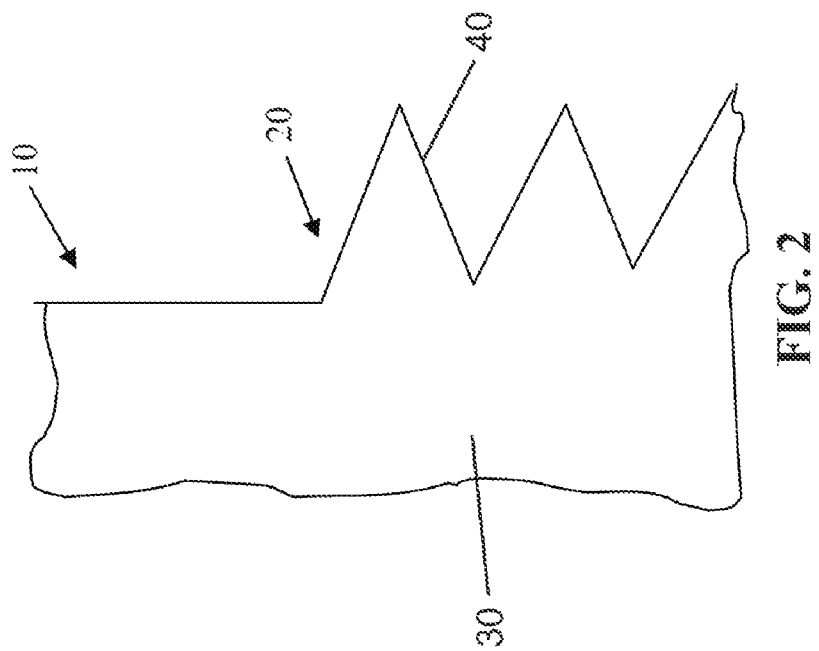
FIG. 2 is a fragmentary view of a portion of the surface of the implant of FIG. 1.
Figure 1:
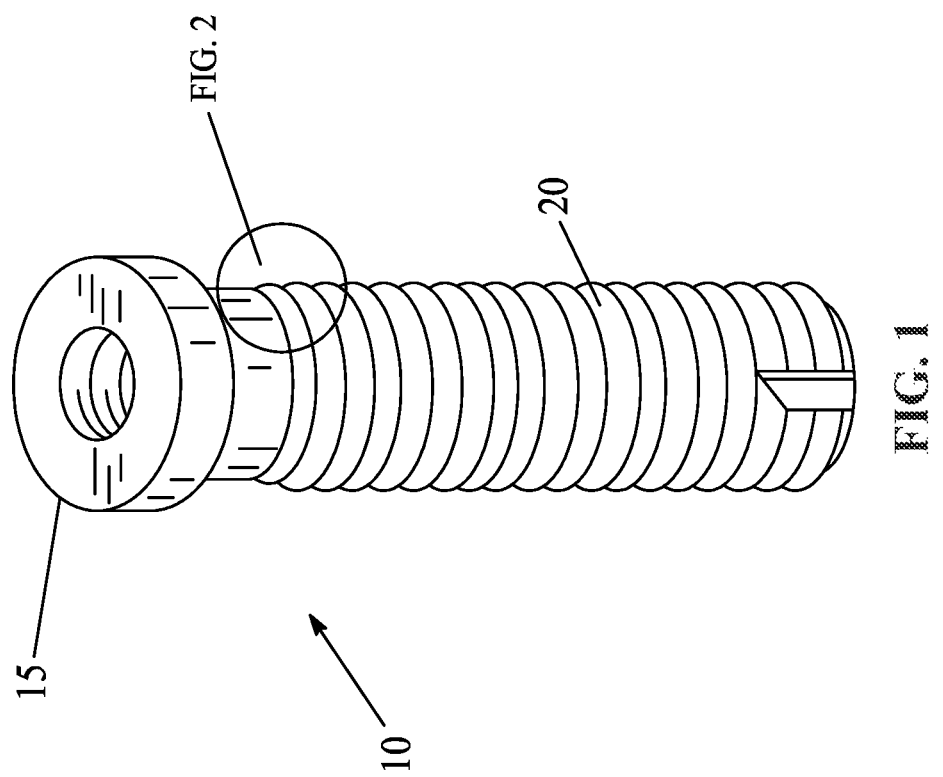
FIG. 1 is a front perspective view of an exemplary dental implant.
Figure 5:
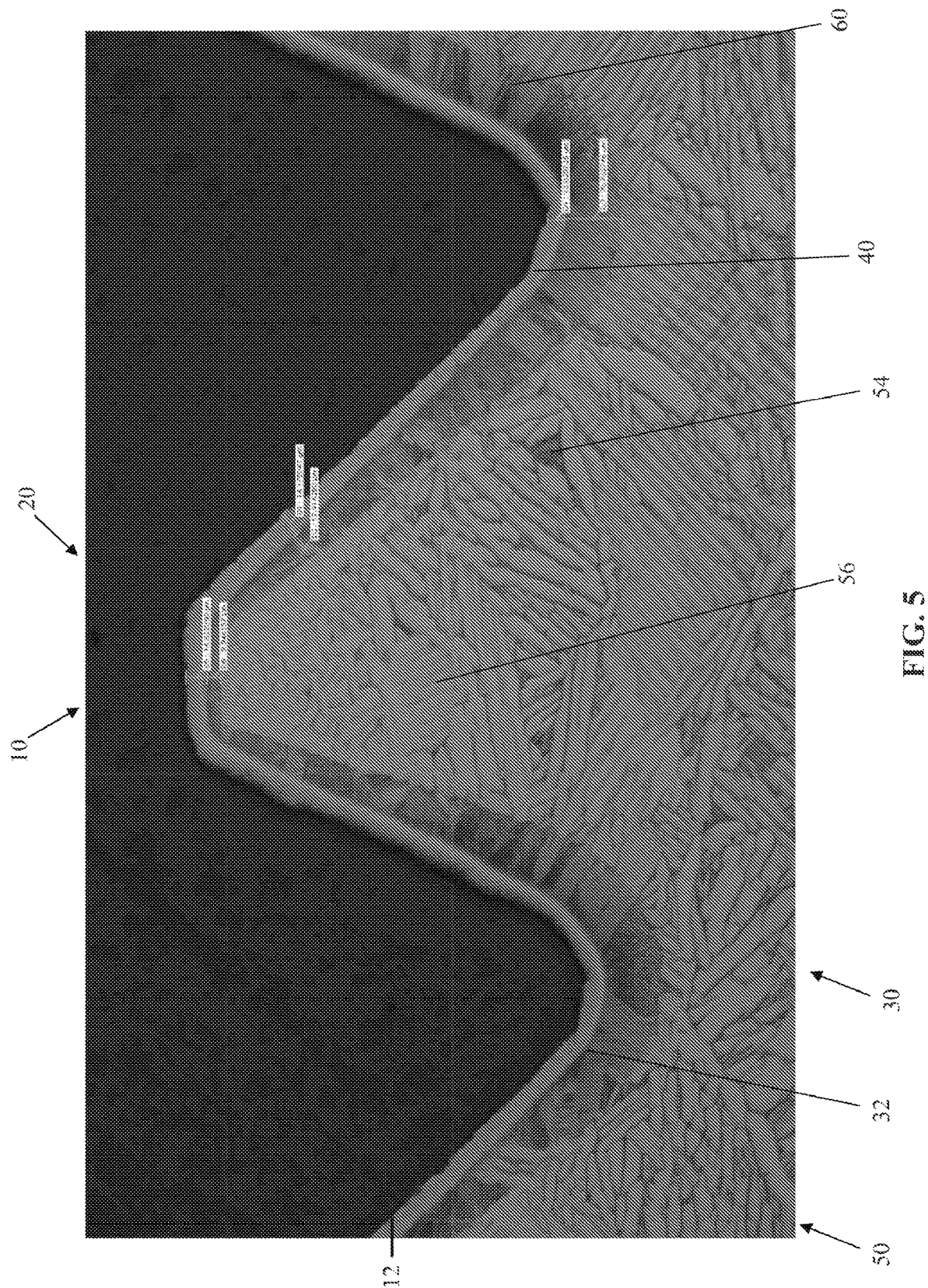
FIG. 5 is a micrograph illustrating the tantalum coating deposited onto the Ti64 substrate following a 10-hour CVD cycle with a furnace set temperature at 850° C.

Referring to FIGS. 1, 2, and 5, an exemplary dental implant 10 includes a head 15 and a shaft having a thread 20, and is formed of a solid substrate 30 and a coating 40 deposited thereon. Illustratively, the implant 10 is a dental implant, though the method of the present disclosure may be used to form coatings on the surfaces of other medical implants. A prosthetic tooth (not shown) may be fixed to the implant 10. The illustrative substrate 30 is comprised of a titanium alloy commonly used to manufacture orthopedic prostheses, specifically Ti-6Al-4V (Ti64). However, the substrate 30 may be formed of other alpha-beta titanium alloys, such as Ti-10-2Fe-3Al, Ti-3Al-2.5V, Ti-5Al-2Sn- 2Zr-6Mo-4Cr, Ti-6Al-2Sn-2Zr-2Mo-2Cr-0.25Si, Ti-6Al-2Sn-4Zr-6Mo, Ti-6Al-4V ELI, Ti-6Al-6V-2Sn-0.75Cu, Ti-7Al-4Mo, Ti-6Al-7Nb, and Ti-8Mn. Alternatively, substrate 30 may be formed of other implantable materials, such as cobalt-chromium-molybdenum alloys and stainless steel. The illustrative coating 40 is pure tantalum or a tantalum alloy, such as tantalum carbide or tantalum nitride. Using chemical vapor deposition (CVD), the coating 40 is deposited onto the substrate 30 in a heated reaction chamber in the manner described below.

Figure 4:
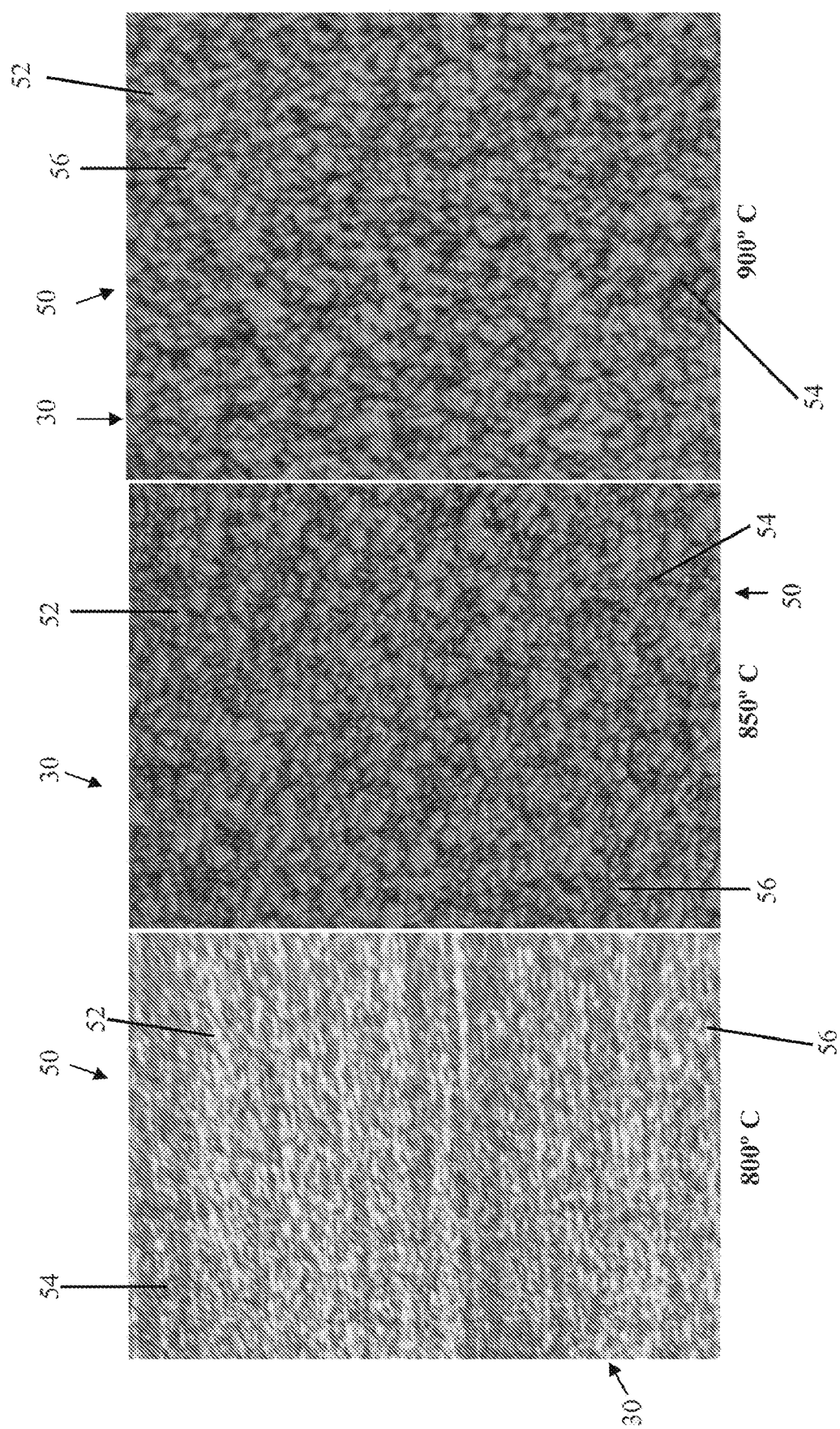
FIG. 4 is a series of micrographs, of the same magnification, illustrating the effect of heat treatment on the microstructure of Ti64.

As shown in FIGS. 3A and 4, the substrate 30 may be formed of a mill-annealed titanium alloy using known metal processing techniques, such as forging or extrusion. Specifically, the titanium alloy comprising the substrate 30 is a binary alloy with a fine-grained microstructure 50 that includes an alpha phase 52 and a beta phase 54. The crystalline microstructure of the alpha phase 52 of the titanium alloy is defined as hexagonal close packed (HCP), whereas the beta phase has a body centered cubic (BCC) crystalline microstructure. Illustratively, the alpha phase 52 is depicted as the lighter regions and the beta phase 54 is depicted in the darker regions.

The alpha phase 52 may have properties similar to a work-hardened titanium alloy, for example increased mechanical strength, relative to the beta phase 54. However, by having both the alpha phase 52 and the beta phase 54, the alpha-beta microstructure 50 of the substrate 30 has both the strength of the alpha phase 52 and the ductility of the beta phase 54. Above certain temperatures, specifically the beta transus temperature, which is between approximately 969° C. (1777° F.) and 989° C. (1813° F.), the titanium alloy may be comprised entirely of the beta phase 54; therefore, the titanium alloy may exhibit decreased mechanical strength relative to the alpha-beta microstructure 50. Additionally, when the temperature of the titanium alloy comprising the substrate 30 is greater than the recrystallization temperature, which is approximately 924° C. (1695° F.), grains 56 within the alpha phase 52 grow and coarsen. Coarse grains also may contribute to decreased mechanical strength of the titanium alloy.

Referring to FIGS. 3A-3D, the tantalum coating 40 may be deposited onto the substrate 30 to provide a textured surface (FIGS. 10A-10B) which, as described below, may promote osseointegration, and/or inhibit biofilm formation. Other suitable biocompatible metals that may be used to coat the substrate 30 include other refractory (Group IV-VI) metals, such as niobium, hafnium, tungsten, and alloys thereof, for example. Despite its biocompatibility and corrosion-resistance, tantalum is not typically used as an implant substrate 30 because the mechanical strength of tantalum is less than that of titanium alloys and other engineered implant substrate materials. Additionally, tantalum is a beta-stabilizer which lowers the beta transus temperature of the titanium alloy and may compromise the mechanical strength of the substrate 30.

Figure 6:
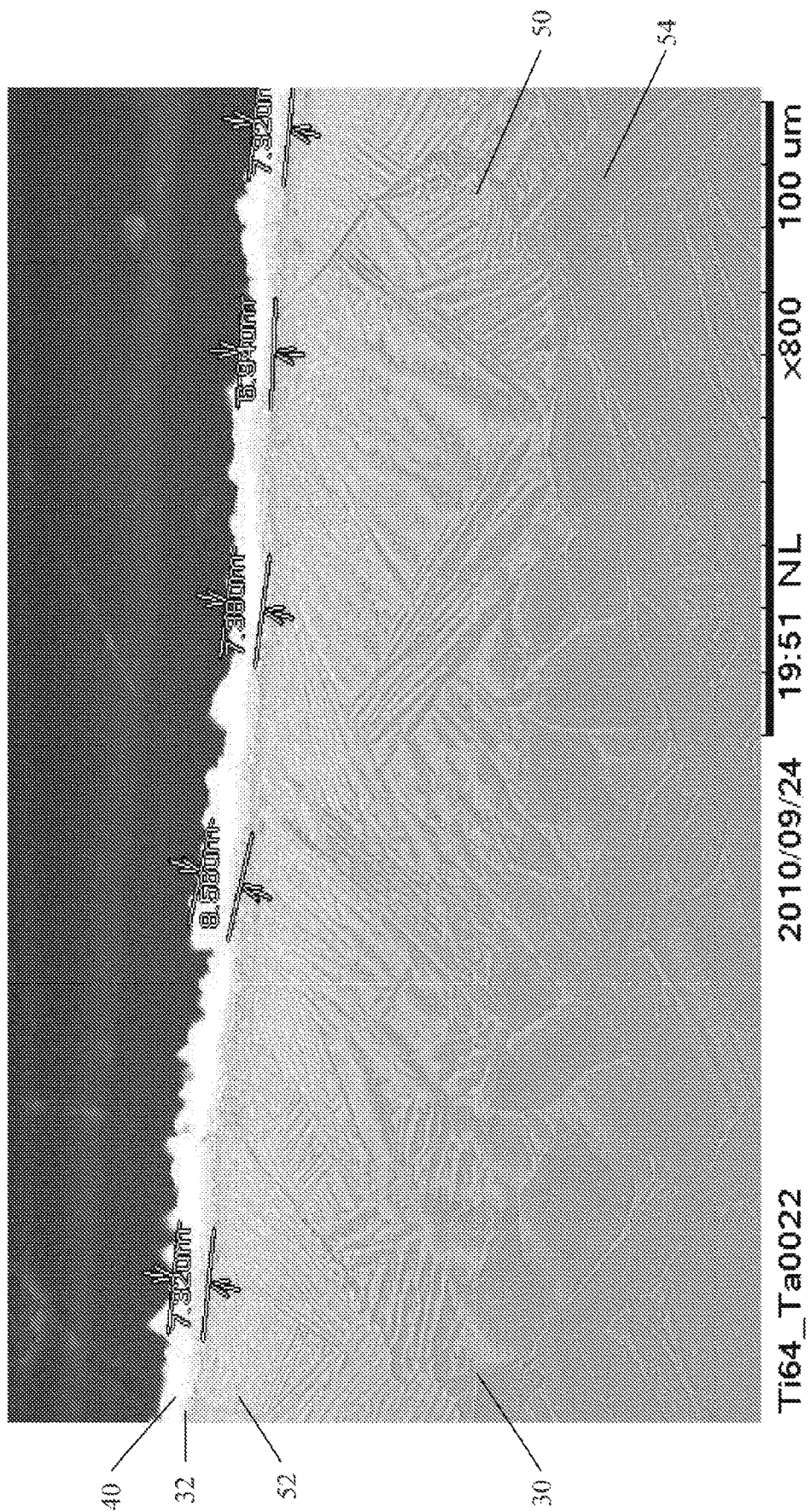
FIG. 6 is a micrograph, at a magnification of 800×, illustrating the tantalum coating deposited onto the Ti64 substrate following a 10-hour CVD cycle with a furnace set temperature at 895° C.
Figure 7:
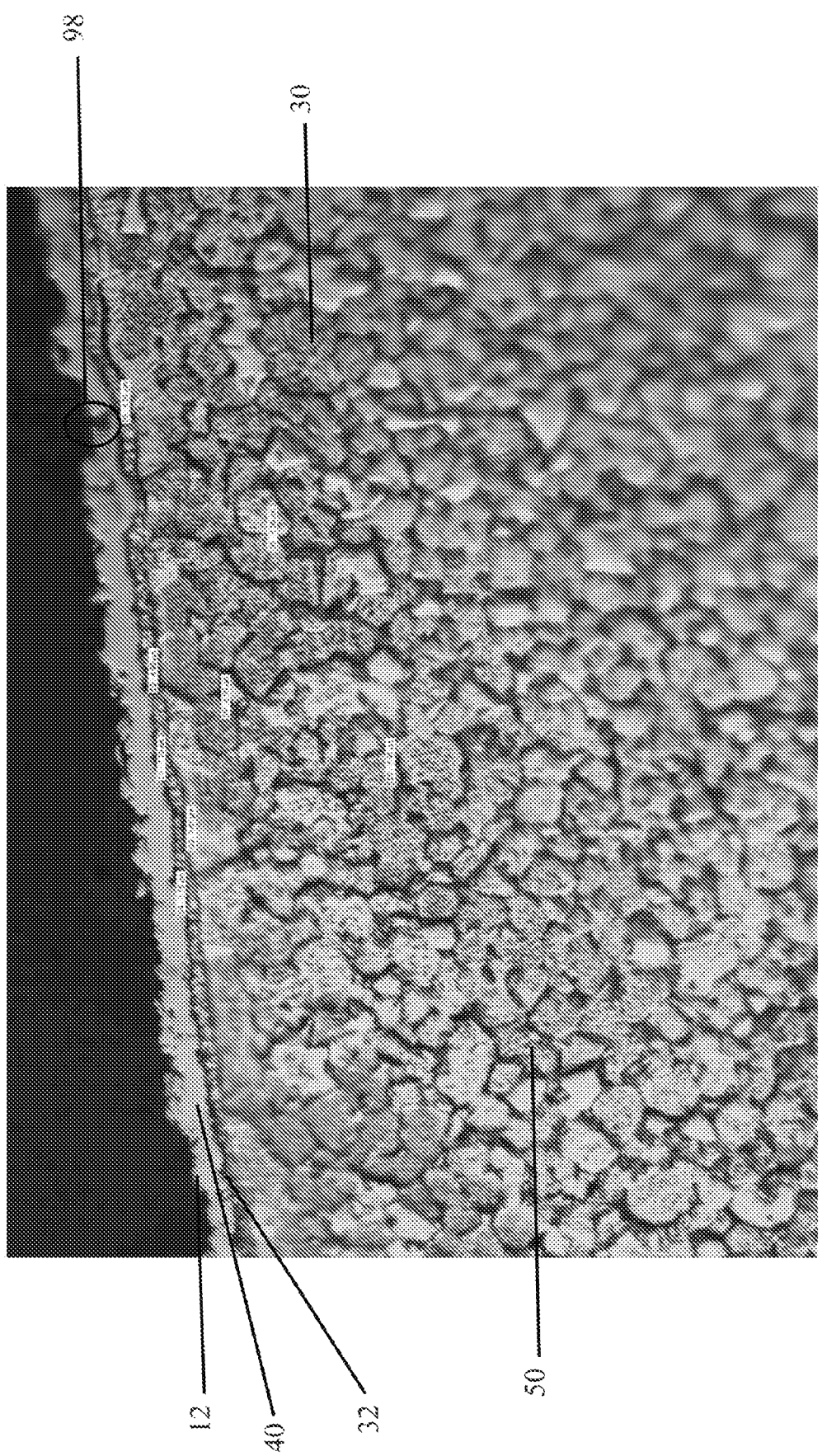
FIG. 7 is a micrograph of the Ti64 substrate having a tantalum coating produced by a 10-hour CVD cycle with a furnace set temperature at 850° C. and the substrate placed in a radiant heat shield box.
Figure 8:
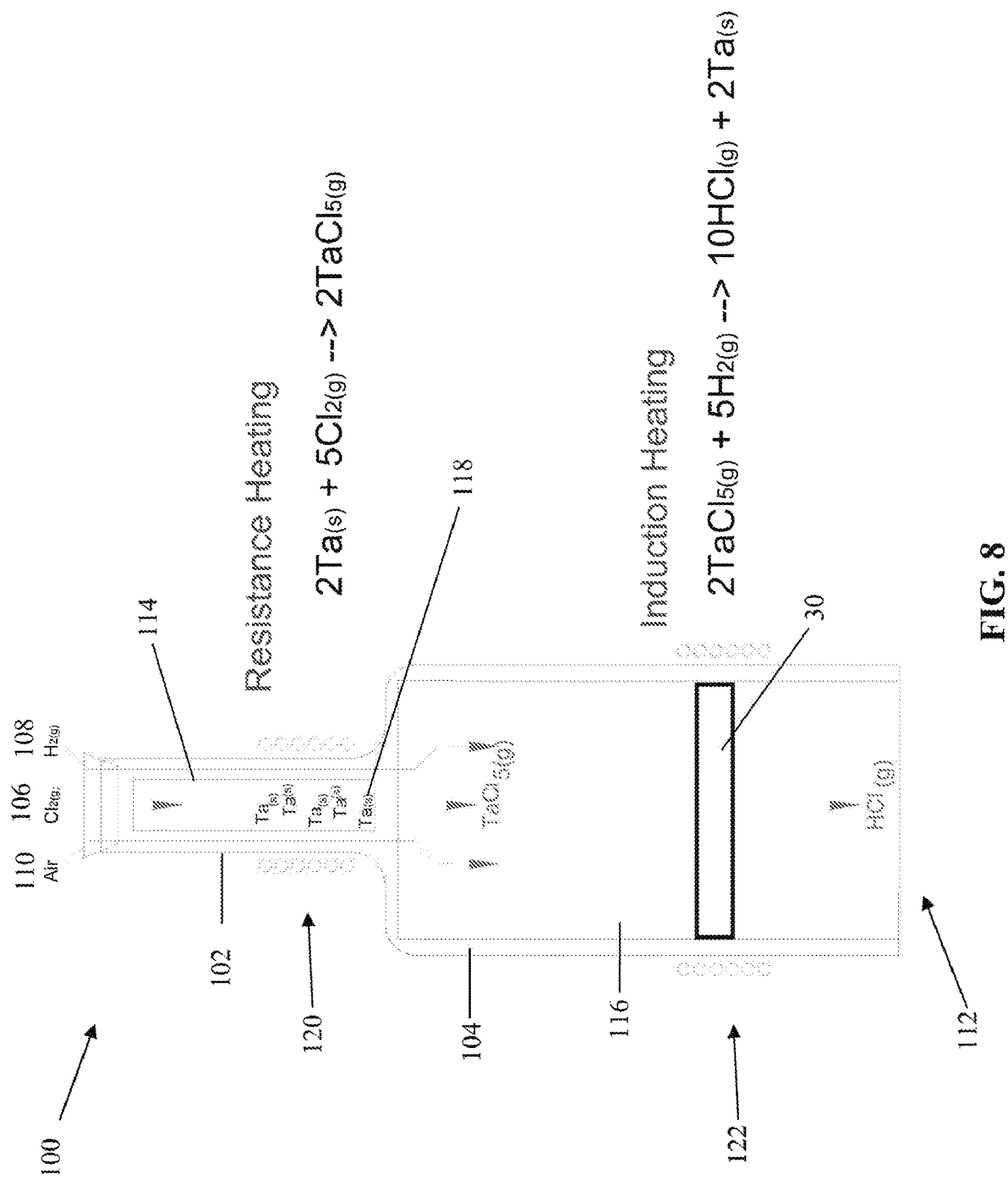
FIG. 8 is a schematic cross-sectional view of a CVD apparatus.

Referring to FIGS. 3A-3D and 5-8, the coating 40 is deposited onto the substrate 30 using the CVD process described hereinafter and in U.S. Pat. No. 5,282,861 to Kaplan, the disclosure of which is expressly incorporated by reference. An apparatus 100 of the type shown in FIG. 8 is provided to perform the CVD process. FIG. 8 is schematic in nature, and it is understood that the design of the apparatus 100 may vary. The apparatus 100 includes a housing 102 that defines the internal reaction chamber 104. The apparatus 100 includes a chlorine gas ($Cl_2$) input 106, a hydrogen gas ($H_2$) input 108, and an air input 110 into the reaction chamber 104. The apparatus 100 also includes an exhaust gas output 112 from the reaction chamber 104. Within the reaction chamber 104, the apparatus 100 includes a heated chlorination chamber 114 and a heated deposition chamber or furnace 116. A supply of tantalum 118 or another biocompatible coating metal is located within the chlorination chamber 114, and the titanium alloy substrate 30 is located within the deposition chamber 116.

In a typical CVD operation, $Cl_2$ gas is injected via the input 106 and $H_2$ gas is injected via the input 108 into the reaction chamber 104. Once inside the heated chlorination chamber 114, which may be resistance-heated by clamshell heater 120 to a temperature of approximately 500° C., the $Cl_2$ gas reacts with tantalum 118 to form tantalum chloride gas, such as tantalum pentachloride ($TaCl_5$), for example. The tantalum chloride gas then mixes with the injected $H_2$ gas and travels into the heated deposition chamber 116, which may be induction-heated by induction coil 122 to a temperature of approximately 900° C.-1,100° C., and more specifically to a temperature of approximately 900° C.-970° C. Once inside the heated deposition chamber 116, the tantalum chloride and $H_2$ gases flow around the substrate 30. Upon contact with the heated surfaces of the substrate 30, the tantalum chloride and $H_2$ gases react to liberate a gaseous hydrogen chloride (HCl) byproduct and deposit tantalum metal onto the substrate 30. The HCl gas is then exhausted via the exhaust gas output 112 from the reaction chamber 104, along with excess reactant gases. As shown in FIG. 6, the tantalum atoms are deposited as a thin, substantially uniform film or coating 40 onto an exterior surface 32 of the substrate 30.

With reference to FIGS. 3A-3D, while a typical CVD process may occur at temperatures of at least 900° C., the exemplary embodiment of the present disclosure limits the temperature within the heated deposition chamber 116 (FIG. 8) to approximately 800° C.-900° C., and more specifically to approximately 800° C.-850° C. In order to maintain the mechanical properties (e.g., fatigue strength) of the substrate 30, tantalum deposition during CVD should occur below approximately 850° C. to avoid phase changes within the alpha-beta microstructure 50 that occur at the recrystallization temperature and the beta transus temperature. Therefore, grain growth within the alpha phase is hindered and the titanium alloy retains the alpha-beta matrix 50 described above.

Referring again to FIG. 8, the temperature within the deposition chamber 116 is monitored using thermocouples (not shown) or other similar devices in order to maintain the mechanical properties of the implant 10 (FIG. 1), which may be affected by the CVD processing temperature. The induction coil 122 may cause a non-uniform temperature profile within the heated deposition chamber 116. For example, if the induction coil 122 is positioned near a middle region of the deposition chamber 116, then the temperature of the middle region may be greater than that of an upper region or a lower region of the deposition chamber 116. A graphite furnace or susceptor is positioned inside the deposition chamber 116 to function as a heating element. The induction coil 122 inductively heats the walls of the furnace in the deposition chamber 116 which transfers radiant heat to the interior of the deposition chamber 116. As such, regions within the deposition chamber 116 may be heated both inductively and radiantly at varying levels, thereby increasing or decreasing the temperature of those regions of the deposition chamber 116 relative to other regions.

Figure 9:
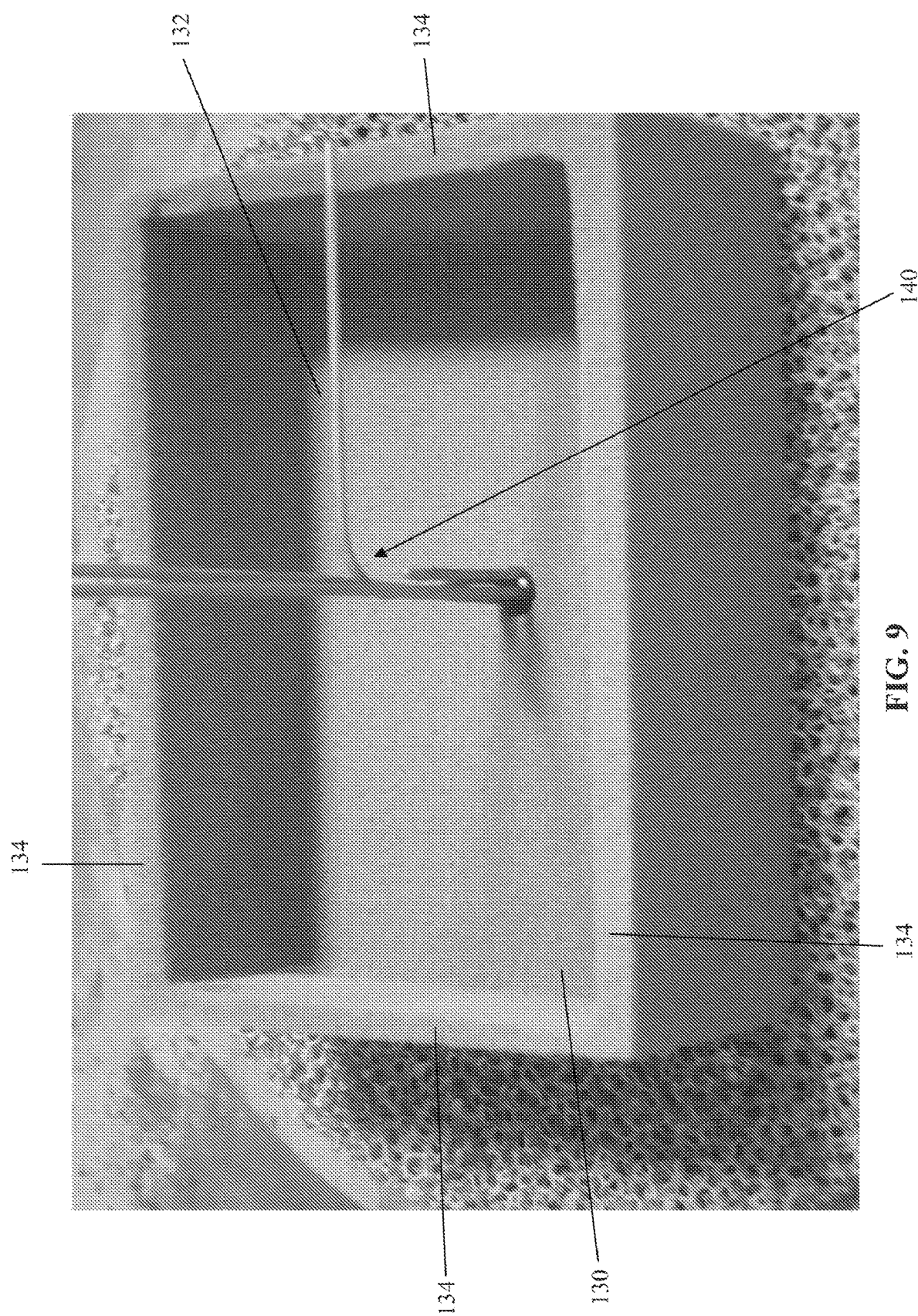
FIG. 9 is a front perspective view of a heat diffuser box supported within the CVD apparatus of FIG. 8.

Referring to FIGS. 7-9, in order to shield the substrate 30 from excess radiant heating and instead, provide more uniform and controlled heating, the heated induction furnace inside the deposition chamber 116 may include a heat diffuser box 130 of the type shown in FIG. 9. The heat diffuser box 130 may be positioned within the deposition chamber 116 adjacent to the induction coil 122 and houses the substrate 30 during the CVD process. The illustrative heat diffuser box 130 shown in FIG. 9 includes a bottom surface 132 and four vertical walls 134, though may be shaped or configured differently. The heat diffuser box 130 may be formed of an open-cell, porous tantalum material, such as Trabecular Metal® technology, generally available from Zimmer, Inc., of Warsaw, Ind. Trabecular Metal® is a registered trademark of Zimmer, Inc., further details of which are disclosed in the above-incorporated U.S. Pat. No. 5,282,861 to Kaplan. The tantalum chloride and hydrogen gases penetrate the pores of the box 130 and contact the substrate 30 in order to complete the deposition reaction. Also, the exemplary embodiment of the heat diffuser box 130 does not include a top surface which further facilitates the deposition reaction. The heat diffuser box 130 attenuates the excess radiant heat from the induction coil 122 and maintains the temperature of the substrate 30 at or above 800° C. and below the metal phase transition temperature of the substrate material, for example, 900° C. As such, the substrate 30 is exposed to controlled inductive and/or radiant heating, which maintains the temperature, and therefore, the microstructural and mechanical characteristics, of the substrate 30. A plurality of thermocouples 140 or other similar devices may be used to monitor the temperature within the heat diffuser box 130.

Referring to FIGS. 3A-3D and 5, when the tantalum coating 40 is deposited onto the titanium alloy substrate 30, a beta-stabilized layer 60 may form at the surface 32 of the substrate 30 between the alpha-beta microstructure 50 and the tantalum coating 40. Height or thickness measurements for such a beta-stabilized layer 60 are shown in FIG. 5 at three separate locations along the substrate 30 although it is difficult to see the measured numbers in FIG. 5 due to the small text size used in the image. As shown in FIG. 5, the approximate thickness of the beta-stabilized layer 60 at these locations were measured as follows: D2=17.414 µm; D3=39.793 µm; and D6=9.948 µm. Since tantalum is a beta-stabilizer, the beta transus temperature of the surface of the substrate 30 may decrease during tantalum deposition, therefore, the concentration of beta phase at the surface 32 of the substrate 30 may increase at temperatures below the beta transus temperature, which is best illustrated in FIG. 3C. However, the thickness of the beta-stabilized layer 60 may advantageously be minimized at the decreased temperatures disclosed herein at which the CVD process is carried out in view of the potential concern that the beta-stabilized layer 60 may decrease the mechanical strength of the implant 10.

Referring to FIGS. 5-7 and 10A-10B, tantalum is deposited onto the substrate 30 at an atomic level, i.e., in an atom-by-atom manner. As additional tantalum atoms deposit onto the previously-deposited tantalum atoms on the surface 32 of the substrate 30, the textured coating 40 forms. Various microscopy techniques, for example scanning electron microscopy (SEM), may be used to illustrate the surface roughness or profile and quantify the thickness of the coating 40. Illustratively, by use of the present process, the thickness of the tantalum deposition coating 40 may be as little as approximately 4, 6, or 8 microns, or as great as approximately 11, 13, or 15 microns, or within any range delimited by any pair of the foregoing values. FIG. 5 also indicates height or thickness measurements for this sort of textured coating although, again, it is difficult to see the measured numbers in FIG. 5 due to the small text size used in the image. The locations of the measurements correspond to those used to measure the beta-stabilized layer 60 as discussed above. The approximate thickness of the textured coating 40 at these locations were measured as follows: D1=14.176 µm; D4=12.021 µm; and D5=14.922 µm. Similarly, FIG. 7 indicates height or thickness measurements for different components of the coated substrate including its tantalum coating and what is effectively a beta-stabilized layer under the coating although, again, it is difficult to see the measured numbers in FIG. 7 due to the small text size used in the image. The approximate thickness of the tantalum coating 40 at location D4 was measured to be 3.75 µm. The approximate thickness of the beta-stabilized layer at location D3 was measured to be 1.81 µm. The approximate thickness of the tantalum coating 40 in combination with the beta-stabilized layer at locations D1, D2 and D5 were measured to be 7.19 µm, 4.90 µm and 4.81 µm, respectively.

Figure 10A:
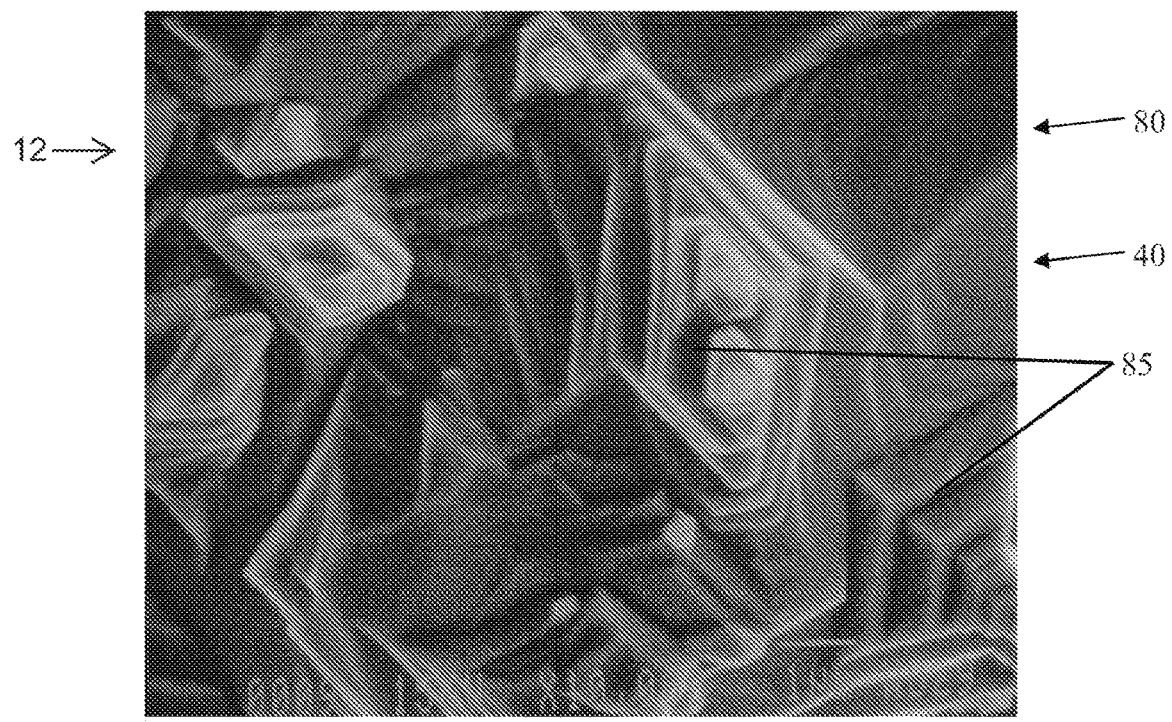
FIG. 10A is a micrograph showing microtexturing of the tantalum coating that has been deposited with a non-angulated CVD microstructure onto the Ti64 substrate.
Figure 10B:
FIG. 10B is a micrograph showing nanotexturing of the tantalum coating that has been deposited with an angulated CVD microstructure onto the Ti64 substrate.
Figure 11:
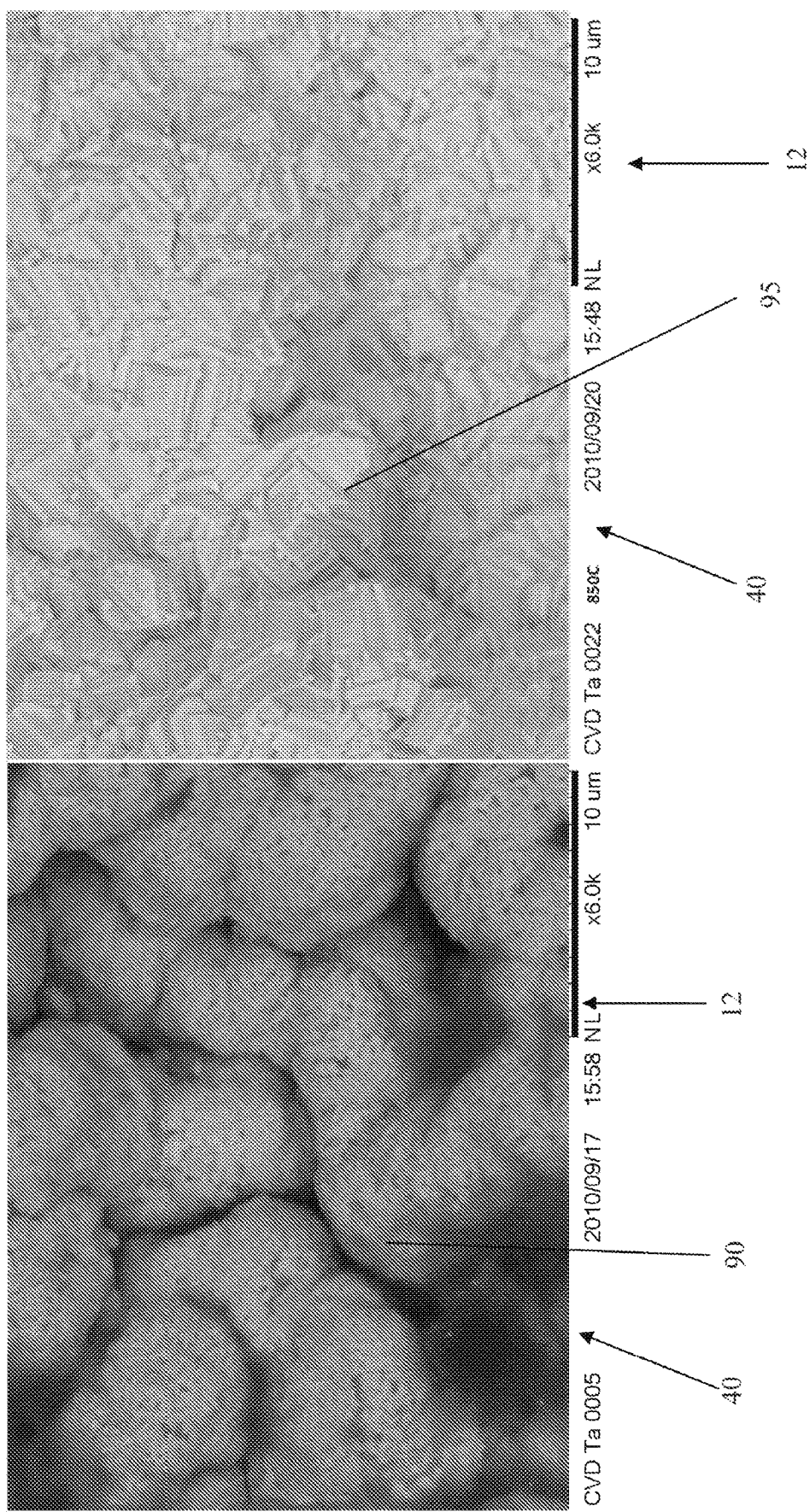
FIG. 11 is a series of micrographs, taken at 6000×, illustrating the effect of temperature on the microtexturing and nanotexturing of the tantalum coating of FIGS. 10A-10B.

With reference to FIGS. 7, 10A-10B, and 11, the tantalum coating 40 of the exemplary implant 10 may exhibit nanometer 70 and/or micrometer-scale surface roughness 80, as shown in FIGS. 10A-10B. Similar to the microstructural characteristics of the substrate 30, the surface profile of the coating 40 is affected by the temperature of the CVD process. As shown to the left in FIG. 11, at lower deposition temperatures, for example 700° C., the coating 40 has a globular, non-angulated surface structure 90. Conversely, at higher deposition temperatures such as 850° C., as shown to the right in FIG. 11, the tantalum coating 40 has an angulated surface structure 95. Furthermore, the tantalum coating 40 may not be continuous along the surface 32 of the substrate 30 and, instead, may include pinholes or defects 98 (FIG. 7). These pinholes 98 expose the substrate 30; however, since both the substrate 30 and the coating 40 are comprised of biocompatible materials, it is not necessary to achieve a completely continuous, pinhole-free coating 40.

The nanotexturing 70 and/or microtexturizing 80 of the coating 40 may prevent bacterial colonization and, therefore, inhibit the formation of a biofilm on the surface of the implant 10 (FIG. 1) after implantation. In particular, when the nanotexturing 70 and/or microtexturing 80 is angulated, as is shown to the right in FIG. 11, nanospaces 75 and microspaces 85 form as striations or channels in the coating 40 and define the angulated textured surface 95. Smaller bacteria cells may "fall" into nanospaces 75 and the microspaces 85 (FIGS. 10A-10B), or the pinholes 98 (FIG. 7) in the coating 40. In this manner, the combination of the nanotexturing 70, microtexturing 80, and pinholes 98 hinders the ability of the bacteria cells to conglomerate and colonize with each other, allowing antibodies to more effectively destroy bacteria cells and decreasing the likelihood that a biofilm will form on a surface 12 of the implant 10.

EXAMPLES

The following non-limiting Examples illustrate various features and characteristics of the present disclosure, which are not to be construed as limited thereto. Throughout the Examples and elsewhere herein, percentages are by weight unless otherwise indicated.

Example 1

Analysis of the Effect of Temperature on the Microstructure of Ti64

Nine samples were prepared, each comprised of mill-annealed Ti64 and shaped as discs. The discs had a radius of 0.5 inch and were cut into two corresponding and substantially identical semi-circular components, each also with a 0.5-inch radius. One of the semi-circular components of each disc pair was heat treated in a furnace for a specified time at a specified temperature. The other corresponding semi-circular component of each disc pair was a "control" and remained at room temperature. The tests included temperatures between 800° C.-900° C. and times between 45-540 minutes, as indicated in Table 1 below.

TABLE 1

Conditions for Heating Treating Ti64

| Test | Time (min.) | Temperature (° C.) |
|---|---|---|
| 1 | 90 | 800 |
| 2 | 60 | 800 |
| 3 | 45 | 800 |
| 4 | 540 | 800 |
| 5 | 60 | 850 |
| 6 | 45 | 900 |
| 7 | 45 | 900 |
| 8 | 45 | 900 |
| 9 | 540 | 900 |

After each test, the grain size of both semi-circular components was measured under the guidelines of ASTM Standard E 112. The grain size (G) is based on the number of grains per square inch at a magnification of 100×, as is represented below in Equation 1:

$$G = \frac{\log \overline{N}_A}{\log 2} + 1.0000 \quad \text{Equation 1}$$

Figure 12:
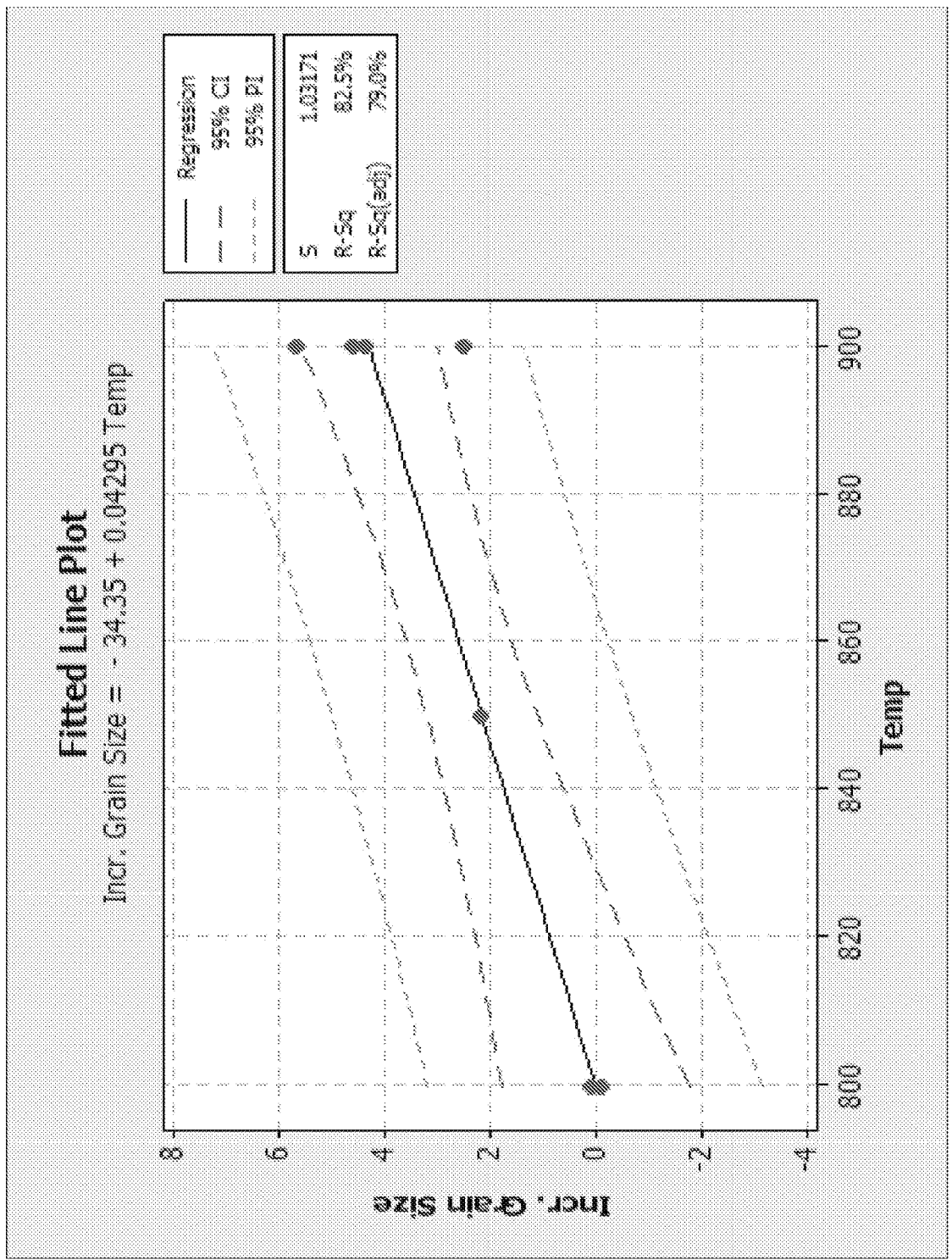
FIG. 12 is a graphical representation of the effect of temperature on the grain size of Ti64.

The grain size of the heat-treated component was compared to the grain size of the control component. A regression analysis was performed to plot the effect of heat treatment, specifically the temperature and time conditions, on the grain size of Ti64. The results, given in Table 2 below and graphically depicted in FIG. 12, indicated that heat treatment increased the average grain size of alpha-beta Ti64. Temperature appeared to have a greater effect on the grain size than did the variable time condition. Specifically, the time of the heat treatment did not appear to consistently affect the grain size of Ti64.

TABLE 2

Effect of Temperature and Time on the Grain Size of Ti64

| Test | Time (min) | Temperature (° C.) | Ti64 Sample | ASTM Grain Size | Mean Grain Diameter (microns) |
|---|---|---|---|---|---|
| 1 | 90 | 800 | Control | 11.6 | 6.9 |
|   |   |   | Heat Treated | 11.7 | 6.8 |
| 2 | 60 | 800 | Control | 12.1 | 5.8 |
|   |   |   | Heat Treated | 10.6 | 10.0 |
| 3 | 45 | 800 | Control | 11.8 | 6.3 |
|   |   |   | Heat Treated | 11.8 | 6.4 |
| 4 | 540 | 800 | Control | 12.0 | 6.9 |
|   |   |   | Heat Treated | 9.7 | 13.3 |
| 5 | 60 | 850 | Control | 12.4 | 5.2 |
|   |   |   | Heat Treated | 11.4 | 7.4 |
| 6 | 45 | 900 | Control | 23.0 | 6.4 |
|   |   |   | Heat Treated | 10.9 | 8.9 |
| 7 | 45 | 900 | Control | 12.3 | 5.5 |
|   |   |   | Heat Treated | 10.2 | 11.2 |

TABLE 2-continued

Effect of Temperature and Time on the Grain Size of Ti64

| Test | Time (min) | Temperature (° C.) | Ti64 Sample | ASTM Grain Size | Mean Grain Diameter (microns) |
|---|---|---|---|---|---|
| 8 | 45 | 900 | Control | 12.0 | 5.9 |
|   |   |   | Heat Treated | 10.4 | 10.3 |
| 9 | 540 | 900 | Control | 11.7 | 6.5 |
|   |   |   | Heat Treated | 10.2 | 11.1 |

Example 2

Analysis of Temperature Dependence on the Thickness of Tantalum Deposition on a Ti64 Substrate Chemical vapor deposition was performed on two samples to determine the effect of temperature on the thickness of the deposition layer. Each sample was a dental implant comprised of mill-annealed, alpha-beta Ti64. The CVD process deposited tantalum onto Ti64 for ten (10) hours. The CVD process for the first sample was conducted at 850° C. (1562° F.) and the CVD process for the second sample was conducted at 895° C. (1643° F.). The thickness of the tantalum coating was measured at various locations along the surface of the implant using known measurement analysis and microscopy techniques. Additionally, micrographs of the implant were taken and visually analyzed to determine the effect of temperature on the microstructure of the substrate of the implant. FIGS. 5-6 depict the thickness of the tantalum layer when a heat diffuser box is not provided within a furnace inside a deposition chamber, even when the furnace has been set to the correct temperature. FIG. 6 shows five separate height or thickness measurements for the tantalum layer along the substrate 30. From left to right, the approximate thickness of the coating was measured as follows: 7.32 μm, 8.56 μm, 7.39 μm, 6.94 μm, and 7.32 μm.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practices in the art to which this disclosure pertains and which fall within the limits of the appended claims.

What is claimed is:

1. A method for depositing a biocompatible material onto an implantable metallic substrate, the method comprising the steps of:
   providing the implantable metallic substrate within a reaction chamber; and
   chemical vapor depositing the biocompatible material onto the implantable metallic substrate at a temperature of between 800° C. and 900° C. so as to form an angulated textured biocompatible coating on the implantable metallic substrate;
   wherein the metallic substrate is a titanium alloy and the titanium alloy retains an alpha-beta microstructure that existed in the titanium alloy before the angulated textured biocompatible coating was formed on the implantable metallic substrate.

2. The method of claim 1, wherein the biocompatible material comprises a metal that includes at least one of tantalum, niobium, hafnium, tungsten, and alloys thereof.

3. The method of claim 1, wherein the angulated textured biocompatible coating has an average thickness of between 4 microns and 15 microns.

4. The method of claim 1, further comprising shielding the implantable metallic substrate from excess heat in the reaction chamber with a heat diffusing structure.

5. The method of claim 4, wherein the heat diffusing structure is porous so as to be penetrable by the biocompatible material within the reaction chamber.

6. A method for depositing a biocompatible material onto an implantable metallic substrate, the method comprising the steps of:
   providing the implantable metallic substrate within a reaction chamber;
   chemical vapor depositing the biocompatible material onto the implantable metallic substrate at a temperature of between 800° C. and 900° C. so as to form an angulated textured biocompatible coating on the implantable metallic substrate; and
   providing pin holes in the angulated textured biocompatible coating, the pin holes exposing the implantable metallic substrate.

7. An implantable device, comprising:
   a metallic substrate; and
   a biocompatible metal deposited on a surface of the metallic substrate to provide an angulated textured metallic coating on the metallic substrate, wherein the angulated textured metallic coating is effective to inhibit a biofilm formation on the implantable device upon implantation of the implantable device in a patient, wherein the metallic substrate a titanium alloy, and wherein the titanium alloy retains an alpha-beta microstructure that existed in the titanium alloy before the angulated textured metallic coating was formed on the metallic substrate.

8. The implantable device of claim 7, wherein the biocompatible metal includes at least one of tantalum, niobium, hafnium, tungsten, and alloys thereof.

9. The implantable device of claim 7, wherein the angulated textured metallic coating has an average thickness of less than 15 microns.

10. The implantable device of claim 7, wherein the angulated textured metallic coating has an average thickness greater than 4 microns.

11. An implantable device, comprising:
   a metallic substrate; and
   a biocompatible metal deposited on a surface of the metallic substrate to provide an angulated textured metallic coating on the metallic substrate, wherein the angulated textured metallic coating is effective to inhibit a biofilm formation on the implantable device upon implantation of the implantable device in a patient, wherein the angulated textured metallic coating includes pin holes exposing the metallic substrate.

12. A method for depositing a biocompatible metal onto an implantable metallic substrate, the method comprising the steps of:
   providing the implantable metallic substrate comprising a titanium alloy within a reaction chamber; and
   chemical vapor depositing the biocompatible metal onto the implantable metallic substrate so as to form an angulated textured metallic coating on the implantable metallic substrate, wherein the biocompatible metal includes at least one of tantalum, niobium, hafnium, tungsten, and alloys thereof;
   wherein the titanium alloy retains an alpha-beta microstructure that existed in the titanium alloy before the angulated textured metallic coating was formed on the implantable metallic substrate.

13. The method of claim 12, wherein the angulated textured metallic coating has an average thickness of between 4 microns and 15 microns.

14. The method of claim 12, further comprising shielding the implantable metallic substrate from excess heat in the reaction chamber with a heat diffusing structure.

15. The method of claim 12, wherein the depositing of the biocompatible metal onto the implantable metallic substrate occurs at a temperature of between 800° C. and 900° C.

* * * * *